(12) United States Patent
Saito et al.

(10) Patent No.: US 9,883,789 B2
(45) Date of Patent: Feb. 6, 2018

(54) FLEXIBLE TUBE FOR ENDOSCOPE, AND ENDOSCOPE

(71) Applicant: OLYMPUS CORPORATION, Hachioji-shi, Tokyo (JP)

(72) Inventors: Kenichiro Saito, Tachikawa (JP); Takahiro Kishi, Yokohama (JP); Naoyuki Hoshi, Aizuwakamatsu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/154,096

(22) Filed: May 13, 2016

(65) Prior Publication Data

US 2016/0249788 A1    Sep. 1, 2016

Related U.S. Application Data

(63) Continuation of application No. PCT/JP2014/081596, filed on Nov. 28, 2014.

(30) Foreign Application Priority Data

Dec. 6, 2013   (JP) ................................. 2013-253476

(51) Int. Cl.
*A61B 1/00* (2006.01)
*A61B 1/005* (2006.01)
(Continued)

(52) U.S. Cl.
CPC ........ *A61B 1/0055* (2013.01); *A61B 1/00071* (2013.01); *A61M 25/005* (2013.01);
(Continued)

(58) Field of Classification Search
CPC ............ A61M 25/0045; A61M 25/005; A61M 25/0053; A61B 1/00071; A61B 1/0055
(Continued)

(56) References Cited

U.S. PATENT DOCUMENTS 4,805,595 A * 2/1989 Kanbara ............ A61B 1/00071
600/140
5,069,674 A * 12/1991 Fearnot ............. A61M 25/0045
604/524

(Continued)

FOREIGN PATENT DOCUMENTS

JP    2002-000551 A    1/2002
JP    2003-334158 A    11/2003
(Continued)

OTHER PUBLICATIONS

Jun. 16, 2016 International Preliminary Report on Patentability issued in PCT Application No. PCT/JP2014/081596.
(Continued)

*Primary Examiner* — Timothy J Neal
*Assistant Examiner* — Aaron B Fairchild
(74) *Attorney, Agent, or Firm* — Oliff PLC

(57) ABSTRACT

A flexible tube for an endoscope includes a helical tube, a cover, and an inhibition mechanism. The inhibition mechanism enables movement of a densely wound portion to the cover in a direction of a central axis of the helical tube and inhibits movement of a loosely wound portion to the cover in the central axis direction of the helical tube.

13 Claims, 15 Drawing Sheets

(51) Int. Cl.
   *A61M 25/00* (2006.01)
   *G02B 23/24* (2006.01)
(52) U.S. Cl.
   CPC .... *A61M 25/0045* (2013.01); *A61M 25/0053* (2013.01); *G02B 23/2476* (2013.01)
(58) Field of Classification Search
   USPC .................................. 600/140; 604/525, 526
   See application file for complete search history.

(56) References Cited

U.S. PATENT DOCUMENTS

| | | | | |
|---|---|---|---|---|
| 6,036,670 | A * | 3/2000 | Wijeratne | A61M 25/005 604/526 |
| 2003/0220543 | A1 | 11/2003 | Abe | |
| 2005/0004433 | A1 * | 1/2005 | Hirata | A61B 1/0055 600/152 |
| 2005/0119525 | A1 * | 6/2005 | Takemoto | A61B 1/00154 600/114 |
| 2007/0060996 | A1 * | 3/2007 | Goodin | A61M 25/005 623/1.11 |
| 2009/0030277 | A1 * | 1/2009 | Fujimoto | A61B 1/00071 600/114 |
| 2013/0112457 | A1 | 5/2013 | Kitagawa | |
| 2013/0144126 | A1 | 6/2013 | Iede | |
| 2014/0155697 | A1 | 6/2014 | Iede | |
| 2014/0188081 | A1 | 7/2014 | Saito et al. | |

FOREIGN PATENT DOCUMENTS

| | | |
|---|---|---|
| JP | 2010-104668 A | 5/2010 |
| JP | 2012-120573 A | 6/2012 |
| JP | 2013-097327 A | 5/2013 |
| WO | 2013/168552 A1 | 11/2013 |

OTHER PUBLICATIONS

Mar. 10, 2015 International Search Report issued in International Patent Application No. PCT/JP2014/081596.

Sep. 8, 2015 Office Action issued in Japanese Patent Application No. 2015-528776.

May 2, 2017 Office Action issued in Chinese Application No. 201480066549.9.

Aug. 17, 2017 extended European Search Report issued in European Application No. 14866931.0.

* cited by examiner

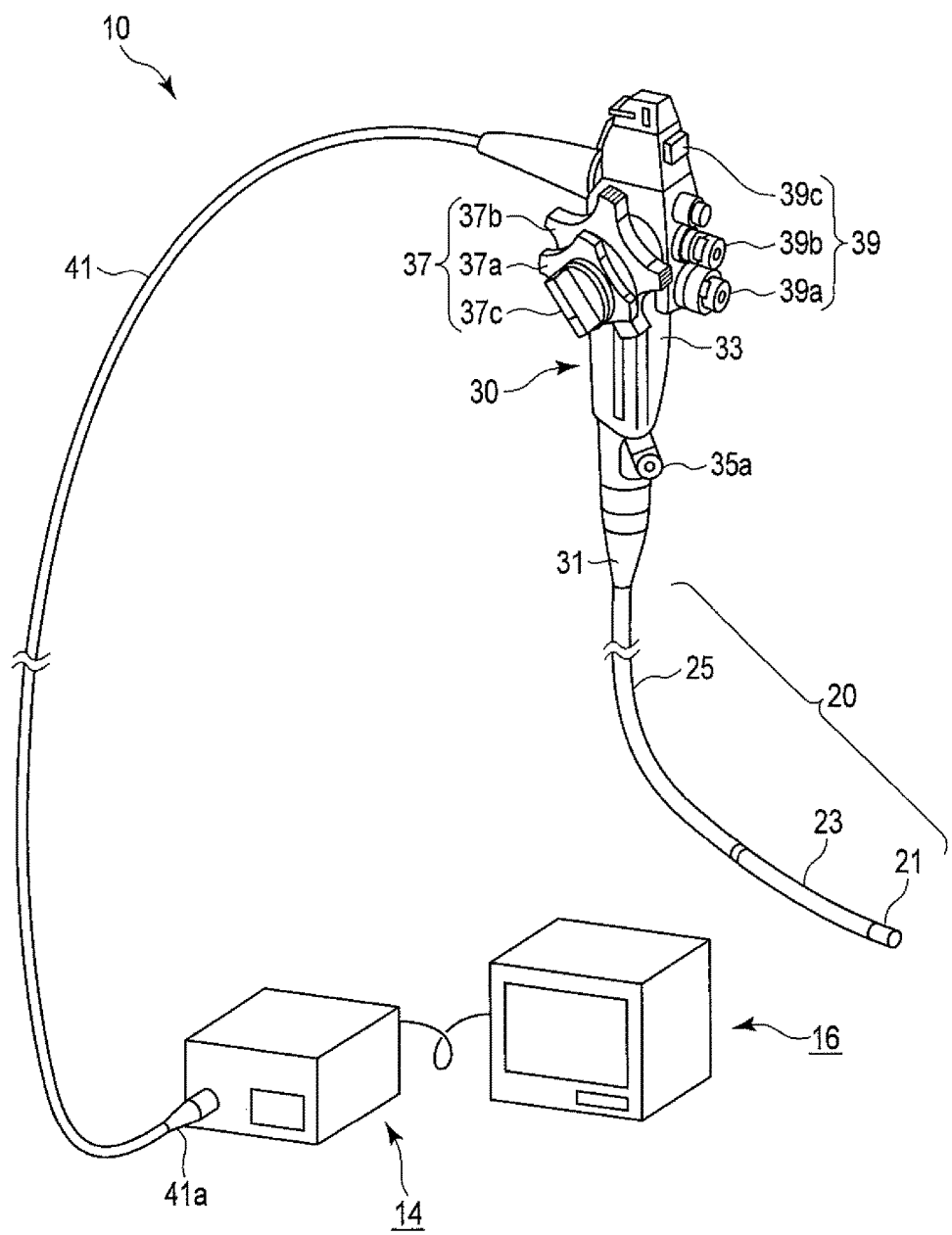
F I G. 1

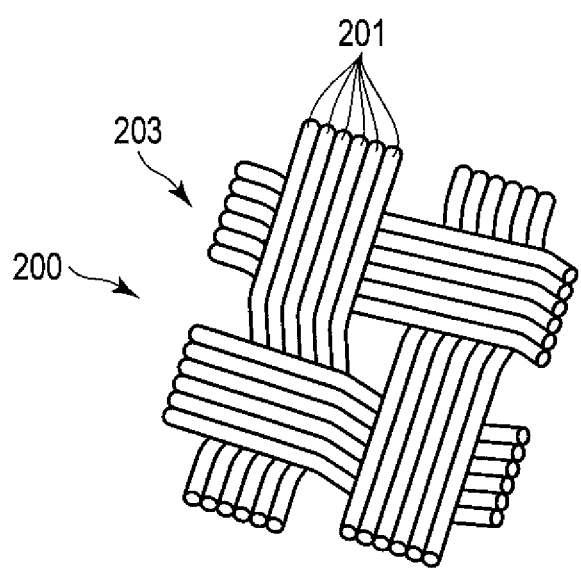
F I G. 3D

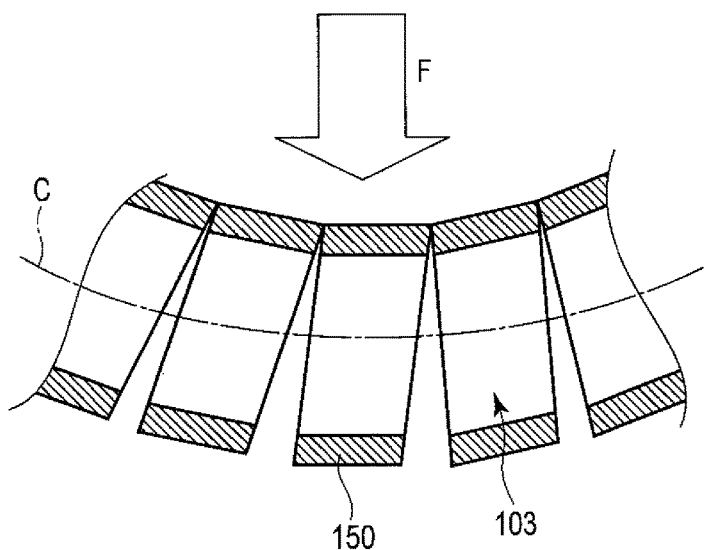
F I G. 5B
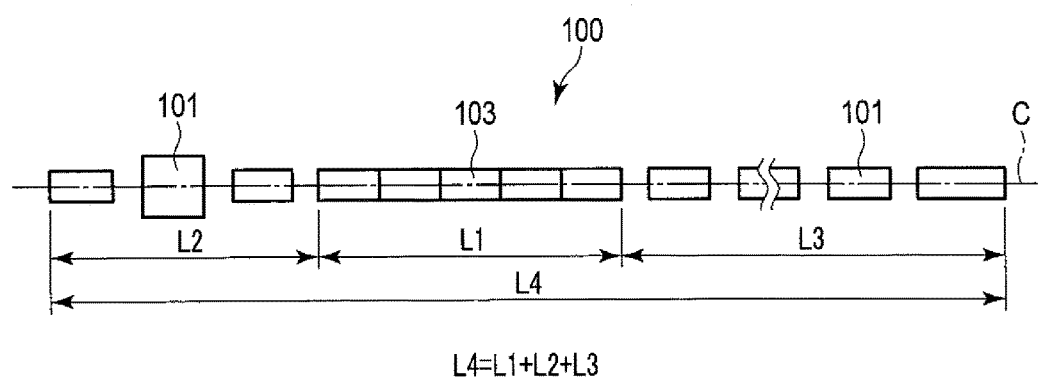
L4=L1+L2+L3
F I G. 5C

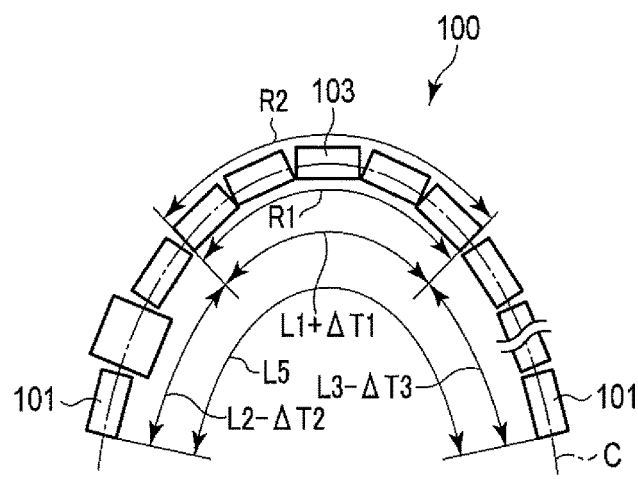
$L5 = L1 + \Delta T1 + L2 - \Delta T2 + L3 - \Delta T3$
$L4 = L5$
$\Delta T1 = \Delta T2 + \Delta T3$
F I G. 5D
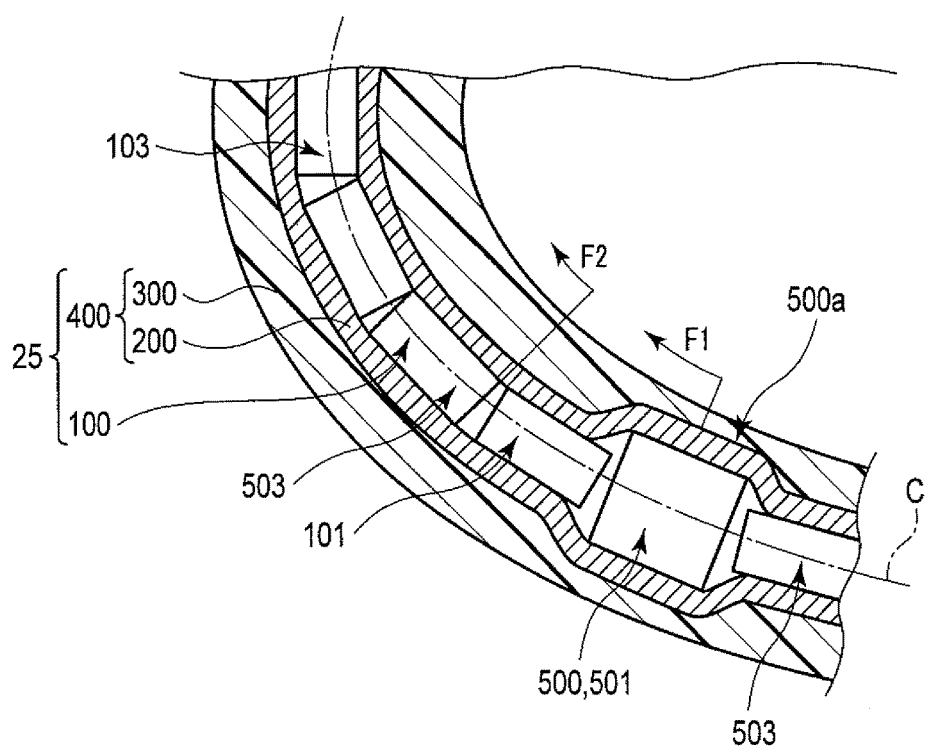
F I G. 6

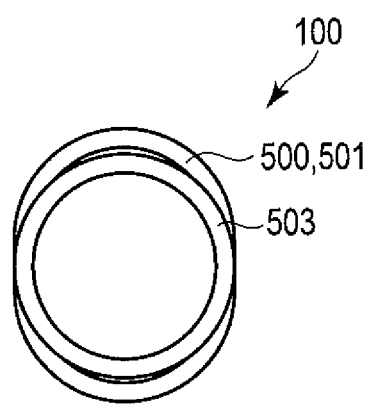
F I G. 7

FLEXIBLE TUBE FOR ENDOSCOPE, AND ENDOSCOPE

CROSS-REFERENCE TO RELATED APPLICATIONS

This application is a Continuation Application of PCT Application No. PCT/JP2014/081596, filed Nov. 28, 2014 and based upon and claiming the benefit of priority from prior Japanese Patent Application No. 2013-253476, filed Dec. 6, 2013, the entire contents of all of which are incorporated herein by reference.

BACKGROUND OF THE INVENTION

1. Field of the Invention

The present invention relates to a flexible tube for an endoscope which has a helical tube, and an endoscope having this flexible tube.

2. Description of the Related Art

When an inserting section of an endoscope is inserted into, for example, a lumen, the inserting section needs to smoothly bend from a distal end portion of the inserting section toward a proximal end portion of the inserting section to reduce a patient's pain and improve insertion-removal properties.

Such a structure is disclosed in, for example, Jpn. Pat. Appln. KOKAI Publication No. 2010-104668, Jpn. Pat. Appln. KOKAI Publication No. 2012-120573 and Jpn. Pat. Appln. KOKAI Publication No. 2002-551.

For example, Jpn. Pat. Appln. KOKAI Publication No. 2010-104668 discloses an endoscope soft portion. This endoscope soft portion has a helical tube, a reticular tube that covers an outer peripheral surface of the helical tube, and an envelope layer that covers an outer peripheral surface of the reticular tube. In the helical tube, an initial tension is given from both sides in a longitudinal direction of the helical tube. An end portion of the reticular tube is fixed to an end portion of the helical tube, and elongation in the longitudinal direction of the helical tube is controlled.

For example, Jpn. Pat. Appln. KOKAI Publication No. 2012-120573 discloses a flexible tube. This flexible tube has a helical tube, a reticular tube that covers an outer peripheral surface of the helical tube, and an envelope that covers an outer peripheral surface of the reticular tube. The helical tube is a helical elastic tube member. The elastic tube member has a dense coil to which an initial tension is at least partially given.

For example, Jpn. Pat. Appln. KOKAI Publication No. 2002-551 discloses a flexible tube for an endoscope in which a bonding force among a helical tube, a braided body and an envelope is strong.

BRIEF SUMMARY OF THE INVENTION

One aspect of a flexible tube for an endoscope of the present invention includes a helical tube that has a central axis and helically wound along the central axis so that loosely wound portions and densely wound portions to which an initial tension is given are alternately disposed, a cylindrical cover that covers an outer peripheral surface of the helical tube and has a flexibility, and an inhibition mechanism that enables movement of the densely wound portion to the cover in a direction of the central axis and inhibits movement of the loosely wound portion to the cover in the central axis direction.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view of an endoscope according to the present invention;

FIG. 3D is an enlarged view of a part of a reticular tube;

FIG. 5B is a schematic longitudinal cross-sectional view showing a state where the densely wound portion is deformed when a force is applied from a side to a central axis of the densely wound portion;

FIG. 5C is a schematic view showing relations among a length of the helical tube, a length of a loosely wound portion and a length of the densely wound portion in a linear state of the helical tube;

FIG. 5D is a schematic view showing relations among the length of the helical tube, the length of the loosely wound portion and the length of the densely wound portion in a bent state of the helical tube;

FIG. 6 is a view to explain that the part inhibits the loosely wound portion from moving to the reticular tube in an axial direction of the helical tube when the flexible tube bends;

FIG. 7 is a view showing that a diameter of the part partially increases as compared with the other part;

DETAILED DESCRIPTION OF THE INVENTION

Figure 2A:
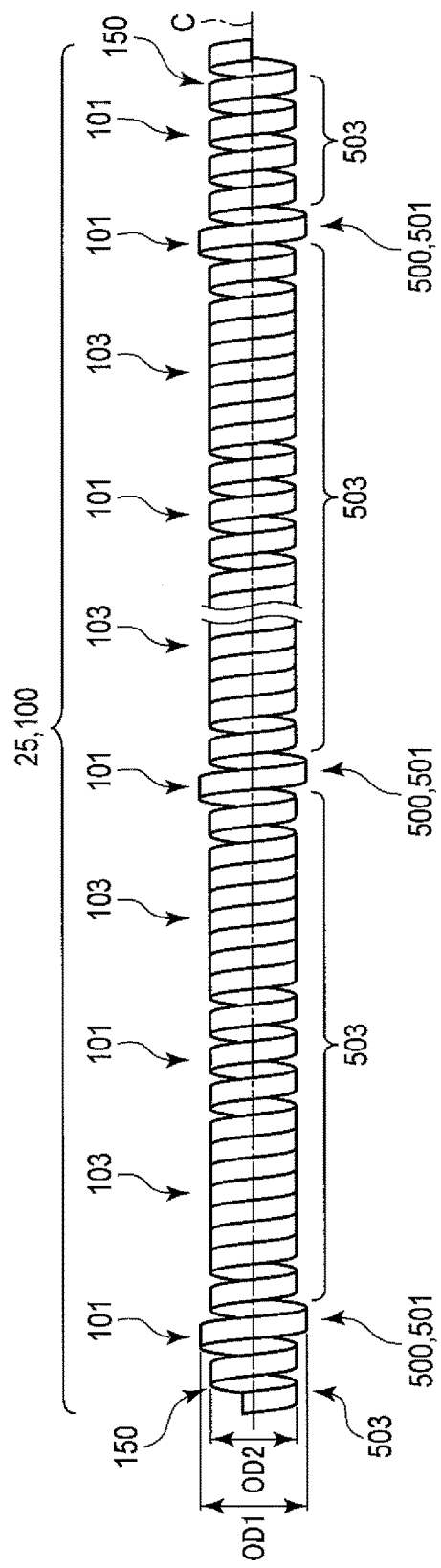
FIG. 2A is a view schematically showing a configuration of a helical tube of a flexible tube.

Hereinafter, embodiments of the present invention will be described in detail with reference to the drawings.

First Embodiment

[Configuration]

A first embodiment will be described with reference to FIG. 1, FIG. 2A, FIG. 2B, FIG. 3A, FIG. 3B, FIG. 3C, FIG. 3D, FIG. 4A, FIG. 4B, FIG. 5A, FIG. 5B, FIG. 5C, FIG. 5D, and FIG. 6.

It is to be noted that in parts of the drawings, drawing of parts of members is omitted or simplified for clarification of the drawing.

[Endoscope 10]

As shown in FIG. 1, an endoscope 10 has a hollow elongated inserting section 20 to be inserted into a lumen such as a body cavity, and an operating section 30 coupled with a proximal end portion of the inserting section 20 to operate the endoscope 10.

[Inserting Section 20]

The inserting section 20 has a distal end hard section 21, a bending section 23, and a flexible tube 25 from a distal end portion side of the inserting section 20 toward a proximal end portion side of the inserting section 20. A proximal end portion of the distal end hard section 21 is coupled with a distal end portion of the bending section 23 and a proximal end portion of the bending section 23 is coupled with a distal end portion of the flexible tube 25. The distal end hard section 21, the bending section 23 and the flexible tube 25 are disposed along a central axis C of the inserting section 20.

[Distal End Hard Section 21]

The distal end hard section 21 is a distal end portion of the inserting section 20, and is hard and does not bend. The distal end hard section 21 has a main body portion (not shown) made of, for example, a stainless steel material or the like, and a cover (not shown) that covers an outer periphery of the main body portion. The main body portion is, for example, hard and columnar. The cover is made of a synthetic resin and has insulating properties.

[Bending Section 23]

The bending section 23 actively bends in a desirable direction such as an upward, downward, right or left direction by an operation of an after-mentioned bending operation portion 37. The bending section 23 bends, whereby a position and an orientation of the distal end hard section 21 change, an observation object is illuminated with unshown illumination light, and the observation object is captured in an observation view field. This observation object is, for example, an affected area, a lesioned area or the like in the subject (e.g., the body cavity).

The bending section 23 has, for example, substantially cylindrical (annular) node rings (not shown). The node rings are arranged in parallel along a direction of the central axis C of the inserting section 20, and the node rings adjacent to each other are rotatably coupled with each other, whereby the bending section is configured to be bendable (rotatable). The node rings adjacent to each other (positioned forward and backward along the central axis C direction of the inserting section 20) are rotatably coupled with each other by an unshown coupling member such as a pin.

Each node ring has an unshown holding member which is disposed on an inner peripheral surface of the node ring and into which an unshown bending wire is inserted to hold the bending wire. The holding member has, for example, a cylindrical shape. The holding member is fixed to the inner peripheral surface of the node ring by, for example, welding. Four holding members are disposed and the holding members are away from each other as much as 90° in a peripheral direction of the node ring. The respective holding members disposed in the node rings are disposed on the same straight line in a longitudinal axis direction of the bending section 23.

A distal end portion of the bending wire is connected to, for example, the distal end hard section 21. The bending wire is inserted into the bending section 23, the flexible tube 25 and a main body section 31. A proximal end portion of the bending wire is connected to the bending operation portion 37. The bending operation portion 37 is operated and the bending wire is pulled, whereby the bending section 23 bends.

It is to be noted that the node ring disposed in the distal end portion of the bending section 23 is coupled with the distal end hard section 21 via a coupling member such as an unshown mouthpiece. The node ring disposed in the proximal end portion of the bending section 23 is coupled with the distal end portion of the flexible tube 25 via a coupling member such as an unshown mouthpiece.

[Flexible Tube 25]

The flexible tube 25 has a desirable flexibility. Therefore, the flexible tube 25 passively bends by receiving an external force F. The external force F indicates a force to be applied to the flexible tube 25 at a desirable angle to a central axis of the flexible tube 25 (the central axis C of the inserting section 20). The flexible tube 25 is a tubular member extended from the after-mentioned main body section 31 in the operating section 30. A configuration of the flexible tube 25 will be described later.

[Operating Section 30]

As shown in FIG. 1, the operating section 30 has the main body section 31 from which the flexible tube 25 is extended, a grasping section 33 that is coupled with a proximal end portion of the main body section 31 and is grasped by an operator who operates the endoscope 10, and a universal cord 41 connected to the grasping section 33.

[Main Body Section 31]

The main body section 31 has a treatment instrument insertion port 35a. The treatment instrument insertion port 35a is coupled with a proximal end portion of an unshown treatment instrument insertion channel. The treatment instrument insertion channel is disposed inside the inserting section 20 and disposed from the flexible tube 25 to the distal end hard section 21. A distal end portion of the treatment instrument insertion channel communicates with an unshown distal end opening portion disposed in the distal end hard section 21. The treatment instrument insertion port 35a is an insertion port through which an unshown treatment instrument for the endoscope is inserted into the treatment instrument insertion channel. The unshown treatment instrument for the endoscope is inserted from the treatment instrument insertion port 35a into the treatment instrument insertion channel, and pushed toward the distal end hard section 21 side. Further, the treatment instrument for the endoscope is projected from the distal end opening portion.

[Grasping Section 33]

The grasping section 33 has the bending operation portion 37 that bends and operates the bending section 23, and a switch portion 39.

[Bending Operation Portion 37]

The bending operation portion 37 has a right/left bending operation knob 37a that bends and operates the bending section 23 to right and left by use of the bending wire, an upward/downward bending operation knob 37b that bends and operates the bending section 23 upward and downward by use of the bending wire, and a fixing knob 37c that fixes a position of the bent bending section 23.

[Switch Portion 39]

The switch portion 39 has a suction switch 39a, a gas sending/water sending switch 39b, and various switches 39c for endoscope photography. The suction switch 39a, the gas sending/water sending switch 39b and the various switches 39c are operated by an operator's hand when the grasping section 33 is grasped by the operator.

The suction switch 39a is operated to make the endoscope 10 suck mucus, fluid or the like from the abovementioned distal end opening portion that also serves as a suction opening portion via the treatment instrument insertion channel that also serves as a suction channel.

For the purpose of acquiring an observation view field of an unshown imaging unit in the distal end hard section 21, the gas sending/water sending switch 39b is operated when the fluid is sent from an unshown gas sending tube and an unshown gas sending/water sending tube, and when the fluid is sent from the unshown water sending tube and the gas sending/water sending tube. The fluid includes water or a gas.

The gas sending tube, the water sending tube and the gas sending/water sending tube are disposed from the inserting section 20 via the main body section 31 and the grasping section 33 to the universal cord 41 inside the endoscope 10.

[Universal Cord 41]

The universal cord 41 has a connecting connector 41a that is attachable to and detachable from a control device 14. The control device 14 controls the endoscope 10. The control device 14 has an image processing section that processes an image imaged by the imaging unit. The control device 14 is connected to a display section 16 that displays the image imaged by the imaging unit.

[Configuration of Flexible Tube 25]

Hereinafter, a configuration of the flexible tube 25 will be described with reference to FIG. 2A and FIG. 2B.

Figure 2B:
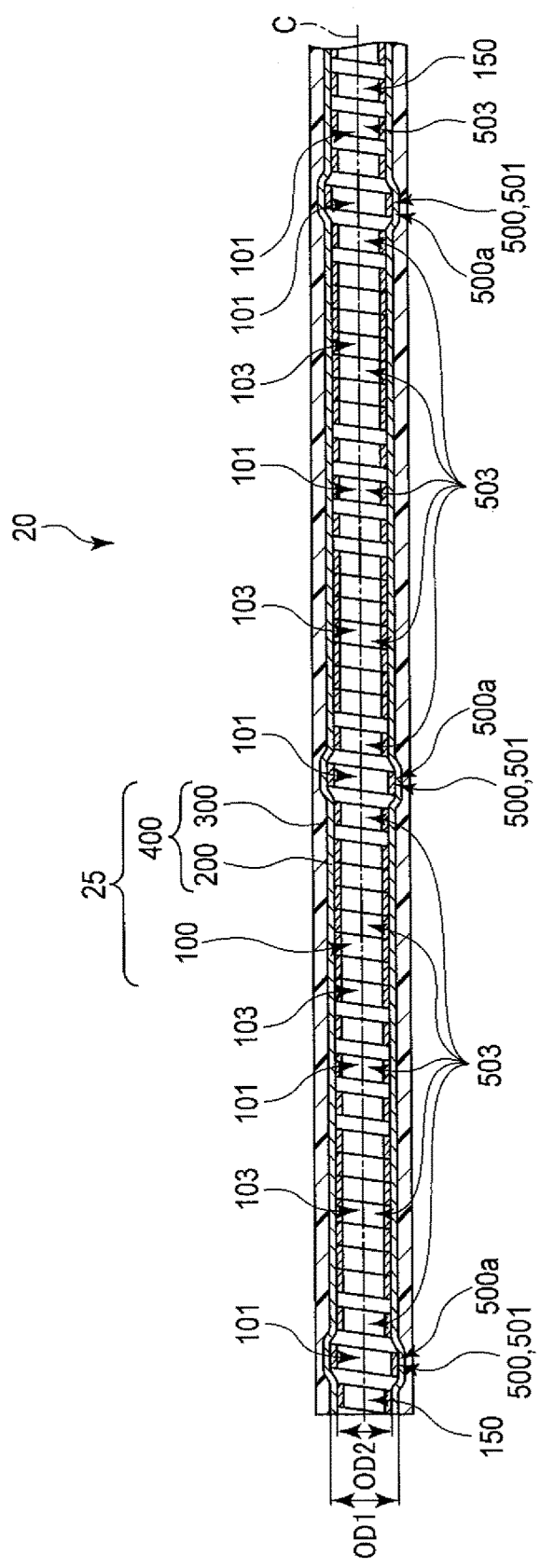
FIG. 2B is a schematically longitudinal cross-sectional view showing a three-layer structure of the flexible tube.

As shown in FIG. 2A and FIG. 2B, the flexible tube 25 has, for example, a hollow shape. As shown in FIG. 2A and FIG. 2B, the flexible tube 25 has, for example, a helical tube 100, a reticular tube 200 that covers an outer peripheral surface of the helical tube 100 so that the reticular tube 200 abuts on the outer peripheral surface of the helical tube 100, and an envelope 300 that covers an outer peripheral surface of the reticular tube 200 so that the envelope 300 abuts on the outer peripheral surface of the reticular tube 200. The reticular tube 200 is laminated on the helical tube 100 and the envelope 300 is laminated on the reticular tube 200.

In this way, the flexible tube 25 is constituted of the helical tube 100, the reticular tube 200 and the envelope 300, and consequently, the flexible tube 25 has a three-layer structure by those. The reticular tube 200 and the envelope 300 have a flexibility. The helical tube 100 is fixed to the reticular tube 200 or the envelope 300 at both ends of the helical tube 100 by using, for example, soldering or bonding.

It is to be noted that the reticular tube 200 does not necessarily have to be disposed. Therefore, the flexible tube 25 may be constituted of at least the helical tube 100 and the envelope 300, and consequently, the flexible tube 25 may have a two-layer structure (not shown) by those.

Therefore, the flexible tube 25 may have the helical tube 100, and a cylindrical cover 400 that has a flexibility and covers the outer peripheral surface of the helical tube 100 so that the cover 400 abuts on the outer peripheral surface of the helical tube 100. The cover 400 has, for example, at least the envelope 300.

[Helical Tube 100]

The helical tube 100 of the present embodiment has a desirable elasticity. This elasticity indicates, for example, a difficulty in bending when the external force is applied in a direction away from the central axis C of the inserting section 20 (e.g., a direction orthogonal to the central axis C), and properties to return the bent helical tube 100 to a substantially original straight state.

As shown in FIG. 2A and FIG. 2B, the helical tube 100 is formed by helically winding, for example, a band-like thin plate member 150 around the central axis C. That is, the helical tube 100 is a helical elastic tube member having an elasticity. It is to be noted that the thin plate member 150 itself is a thin and elongated flat plate member having a rectangular shape. The thin plate member 150 is made of, for example, a stainless steel material or the like.

Figure 3A:
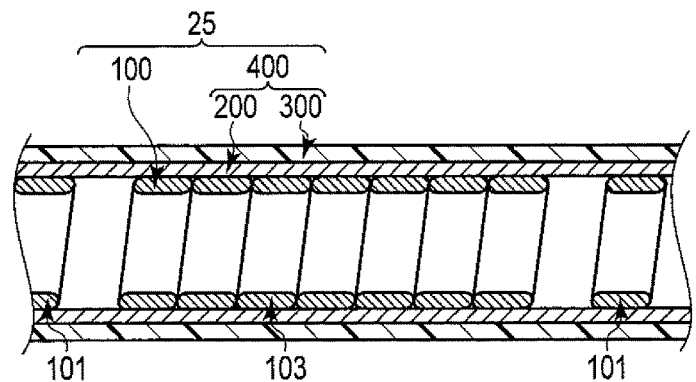
FIG. 3A is a longitudinal cross-sectional view showing the three-layer structure of the flexible tube in a state where a thin plate member of the helical tube has an elongated circular cross section.
Figure 3B:
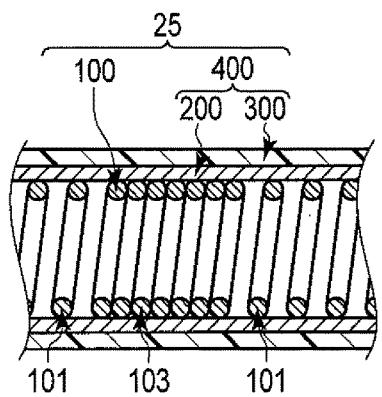
FIG. 3B is a longitudinal cross-sectional view showing the three-layer structure of the flexible tube in a state where the thin plate member of the helical tube has a circular cross section.
Figure 3C:
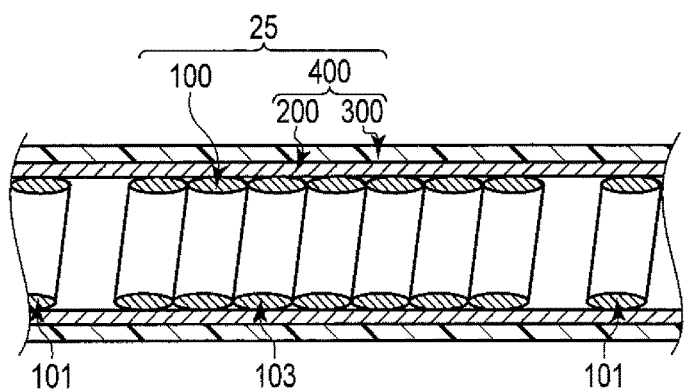
FIG. 3C is a longitudinal cross-sectional view showing the three-layer structure of the flexible tube in a state where the thin plate member of the helical tube has an elliptic cross section.

For a transverse cross section of the thin plate member 150, various shapes are possible; for example, a rectangular shape shown in FIG. 2B, an elongated circular shape shown in FIG. 3A, a substantially circular shape shown in FIG. 3B, an elliptic shape shown in FIG. 3C and the like. Hereinafter, description will be made by defining that the transverse cross section has a rectangular shape shown in FIG. 2A. A detailed configuration of the helical tube 100 will be described later.

[Reticular Tube 200]

As shown in FIG. 3D, the reticular tube 200 is formed by braiding, for example, a strand bundle 203 in which strands 201 made of a stainless steel material are bundled, into a substantially circular tube shape. In the reticular tube 200, the strand bundles 203 intersect with one another in the form of a lattice.

[Envelope 300]

The envelope 300 is formed into a substantially circular tube shape so that the envelope 300 covers the outer peripheral surface of the reticular tube 200.

The envelope 300 is made of, for example, two or more types of resin materials. For example, the resin materials have different hardnesses. The envelope 300 has, for example, a thermoplastic elastomer such as polyurethane or polyester, and a coating layer that coats the outside of this. The hardness of the envelope 300 is desirably adjusted by changing, for example, blend amounts of the resin materials. The envelope 300 may be made of a resin material such as a rubber material, the resin material has a flexibility.

[Configuration of Helical Tube 100]

As shown in FIG. 2A and FIG. 2B, the helical tube 100 has loosely wound portions 101 and densely wound portions 103 to which an initial tension is given along the central axis C direction. Each of the densely wound portions 103 has a distal end portion and a proximal end portion, the distal end portion is integrally connected to one loosely wound portion 101, and the proximal end portion is integrally connected to the other loosely wound portion 101. Further, the helical tube 100 has alternate loosely wound portions 101 and densely wound portions 103 in order from a distal end of the helical tube 100 toward a proximal end of the helical tube 100. Therefore, the helical tube 100 is helically wound along the central axis C so that the loosely wound portions 101 and the densely wound portions 103 are alternately disposed. In other words, the densely wound portion 103 is sandwiched between the loosely wound portions 101 along the central axis C of the helical tube 100, and is adjacent to the loosely wound portions 101 at the distal end portion of the densely wound portion 103 and the proximal end portion of the densely wound portion 103, respectively.

The loosely wound portions 101 are disposed in a distal end portion of the helical tube 100 and a proximal end portion of the helical tube 100. The loosely wound portion 101 disposed in the distal end portion of the helical tube 100 is coupled with the bending section 23 via a coupling member. The loosely wound portion 101 disposed in the proximal end portion of the helical tube 100 is integrally connected to the main body section 31.

The loosely wound portions 101 and the densely wound portions 103 are alternately disposed along the central axis C direction of the helical tube 100. When this configuration is achieved, there is no special restriction on the number of the loosely wound portions 101 and the number of the densely wound portions 103.

As shown in FIG. 2A and FIG. 2B, the helical tube 100 having the loosely wound portions 101 and the densely wound portions 103 is formed by helically winding the thin plate members 150. The loosely wound portions 101 and the densely wound portions 103 are integrally formed by using the same thin plate member 150.

As shown in FIG. 2A and FIG. 2B, the densely wound portion 103 is formed so that the thin plate members 150 adjacent to each other in an axial direction of the helical tube 100 come in contact closely with each other to eliminate a clearance portion therebetween by using the abovementioned initial tension. That is, in the densely wound portion 103, the thin plate members 150 come in close contact with each other in the axial direction of the helical tube 100.

On the other hand, as shown in FIG. 2A and FIG. 2B, in the loosely wound portion 101 to which the initial tension is not given, the loosely wound portion 101 is formed by disposing the thin plate members 150 away from each other in the axial direction of the helical tube 100 to dispose the clearance portion between the members in the axial direction of the helical tube 100. That is, in the loosely wound portion 101, the thin plate members 150 do not come in close contact with each other in the axial direction of the helical tube 100. In the central axis C direction of the inserting section 20, lengths of the clearance portions are, for example, uniform with each other.

Both of the loosely wound portion 101 and the densely wound portion 103 have an elasticity. The elasticity of the densely wound portion 103 is complemented, because the initial tension is given to the densely wound portion 103. Therefore, the elasticity of the densely wound portion 103 is higher than the elasticity of the loosely wound portion 101. Consequently, as to the elasticity of the densely wound portion 103, bouncing properties are strong due to the initial tension as compared with the loosely wound portion 101. In other words, the elasticity of the loosely wound portion 101 is lower than the elasticity of the densely wound portion 103, because the initial tension is not given to the loosely wound portion 101. Therefore, as to the elasticity of the loosely wound portion 101, the bouncing properties are weak as compared with the densely wound portion 103. The elasticities of the densely wound portions 103 are, for example, about the same to each other. The elasticities of the loosely wound portions 101 are, for example, about the same to each other.

The one loosely wound portion 101 has a length of, for example, 25 mm to 50 mm, and the one densely wound portion 103 has a length of, for example, 50 mm to 150 mm. It is to be noted that the length of the loosely wound portion 101 is determined in accordance with an elongation amount of the densely wound portion 103 when the flexible tube 25 bends.

[Inhibition Mechanism 500]

As shown in FIG. 2A, FIG. 2B, FIG. 4A and FIG. 4B, the flexible tube 25 further has an inhibition mechanism 500 that enables movement of at least one densely wound portion 103 to the cover 400 in a central axis direction of the helical tube 100 and inhibits movement of at least one loosely wound portion 101 to the cover 400 in the central axis direction of the helical tube 100, when the flexible tube 25 bends. In detail, the inhibition mechanism 500 inhibits the loosely wound portion 101 from sliding in the cover 400 in the axial direction of the helical tube 100. In this case, the cover 400 indicates, for example, the reticular tube 200.

Here, one example of the inhibition mechanism 500 will be described below with reference to FIG. 2A, FIG. 2B, FIG. 4A and FIG. 4B.

Figure 4A:
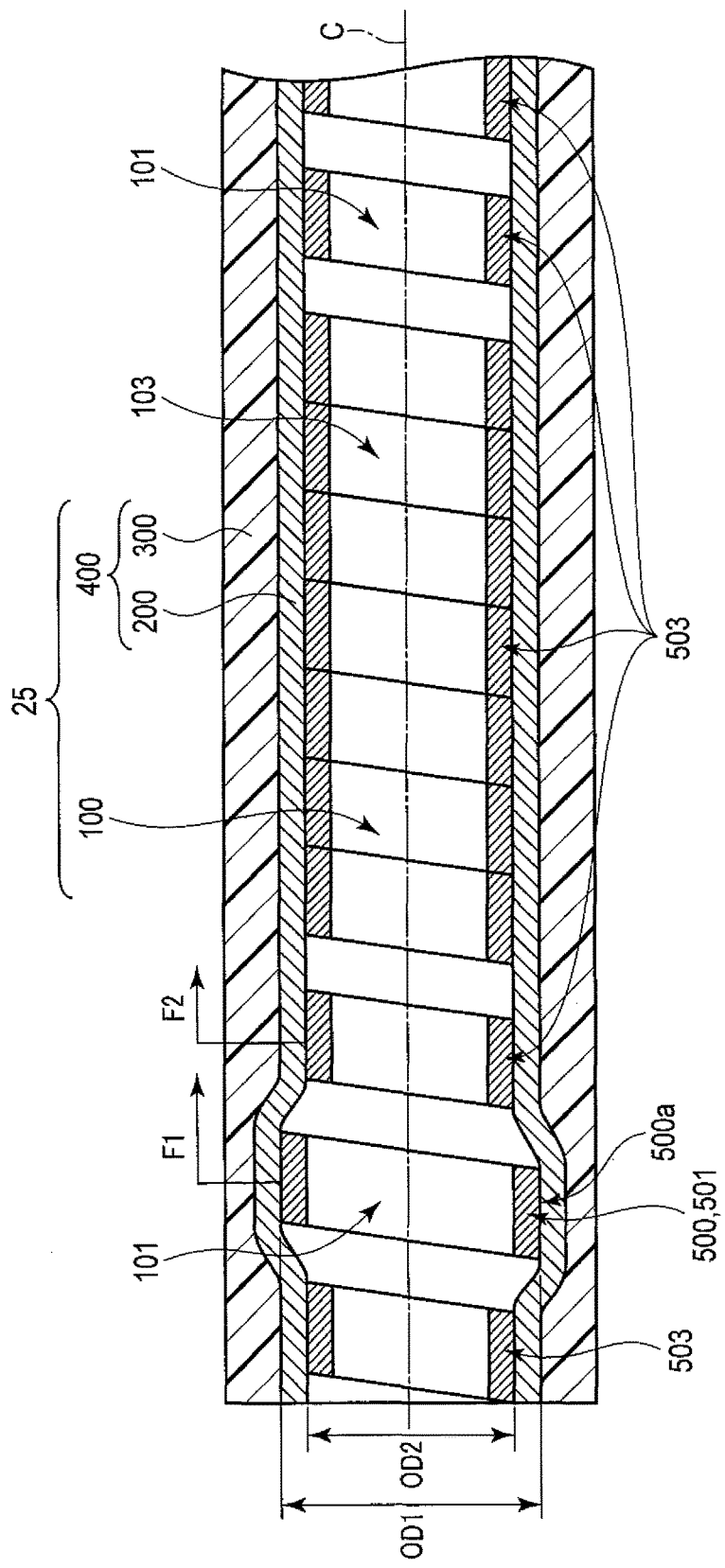
FIG. 4A is an enlarged view of a part of FIG. 2B to explain an inhibition mechanism.

As shown in FIG. 4A, a frictional force generated between an outer peripheral surface of at least a part 501 of the loosely wound portion 101 and an inner peripheral surface of the reticular tube 200 in a portion that covers the outer peripheral surface of the part 501 so that the reticular tube 200 abuts on the outer peripheral surface of the part 501 is referred to as a part frictional force F1. The part frictional force F1 indicates, for example, a force in the axial direction of the helical tube 100. The outer peripheral surface and the inner peripheral surface function as a part frictional force generating section 500a that generates the part frictional force F1. Further, the inhibition mechanism 500 has the part frictional force generating section 500a.

As shown in FIG. 2A, FIG. 2B and FIG. 4A, the part 501 includes, for example, at least one of the loosely wound portions 101 disposed in the distal end portion of the helical tube 100 and the proximal end portion of the helical tube 100. The part 501 is disposed, for example, in every other loosely wound portion 101 to the loosely wound portions 101. Needless to say, the parts 501 may be disposed in all the loosely wound portions 101, or may be disposed at intervals of two loosely wound portions 101, and there is no special restriction on a position at which the part 501 is disposed. The part 501 includes, for example, at least a center portion of the loosely wound portion 101 in the axial direction of the helical tube 100. That is, the inhibition mechanism 500 inhibits at least the center portion of the loosely wound portion 101 in the central axis C direction from moving to the cover 400 in the central axis C direction. The part 501 indicates, for example, one winding of the thin plate member 150. There is no special restriction on the number of the windings. For example, at least the part 501 is disposed in one of the loosely wound portions 101. Therefore, the parts 501 may be disposed in every other winding, for example, in a first winding, a third winding and a fifth winding.

As shown in FIG. 4A, a frictional force generated between an outer peripheral surface of another part 503 except the part 501 in the helical tube 100 and the inner peripheral surface of the reticular tube 200 in a portion that covers the outer peripheral surface of the other part 503 so that that the reticular tube 200 abuts on the outer peripheral surface of the other part 503 is referred to as another part frictional force F2. The other part frictional force F2 indicates, for example, the force in the axial direction of the helical tube 100.

The other parts 503 except the parts 501 in the helical tube 100 include, for example, the other part of the loosely wound portion 101 and the whole densely wound portion 103.

In the inhibition mechanism 500, the part frictional force F1 is larger than the other part frictional force F2.

Figure 4B:
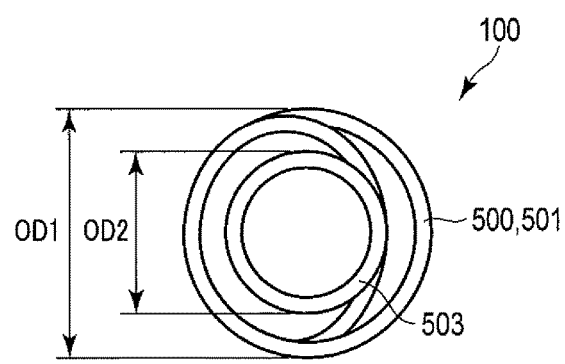
FIG. 4B is a view showing that a cross-sectional shape of a part is analogous to a cross-sectional shape of another part so that the cross-sectional shape of the part is larger than the cross-sectional shape of the other part.

As shown in FIG. 2A, FIG. 2B, FIG. 4A and FIG. 4B, for example, an outer diameter OD1 which the part 501 has is larger than an outer diameter OD2 which the other part 503 has, in a state where, for example, a thickness of the reticular tube 200 is uniform along the total length of the reticular tube 200 as one example. As shown in FIG. 4B, a cross-sectional shape of the part 501 is analogous to a cross-sectional shape of the other part 503 so that the cross-sectional shape of the part 501 is larger than the cross-sectional shape of the other part 503. A cross section of the part 501 and a cross section of the other part 503 have, for example, a circular shape.

As shown in FIG. 4A, in this case, for example, both the part 501 and the other part 503 abut on the reticular tube 200 so that the envelope 300 presses the reticular tube 200 toward the helical tube 100. However, the outer diameter OD1 is larger than the outer diameter OD2, and hence an amount of the force to be applied from the reticular tube 200 to the part 501 is larger than an amount of the force to be applied from the reticular tube 200 to the other part 503. Therefore, the part frictional force F1 is larger than the other part frictional force F2.

It is to be noted that, although not shown, the part 501 may abut on the reticular tube 200 and the other part 503 may not abut on the reticular tube 200. Consequently, the part frictional force F1 is generated, but the other part frictional force F2 is not generated, and the part frictional force F1 is larger than the other part frictional force F2 that is zero.

Further, the part frictional force F1 is larger than the other part frictional force F2, and hence in the central axis C direction, the inhibition mechanism 500 enables the movement of the densely wound portion 103 to the cover 400 rather than the movement of the loosely wound portion 101 to the cover 400. In other words, the part frictional force F1 is larger than the other part frictional force F2, and hence in the central axis C direction, the inhibition mechanism 500 controls the movement of the loosely wound portion 101 to the cover 400 more than the movement of the densely wound portion 103 to the cover 400.

[Initial Tension]

Here, the initial tension applied to the densely wound portion 103 for use in the present embodiment will be described.

Figure 5A:
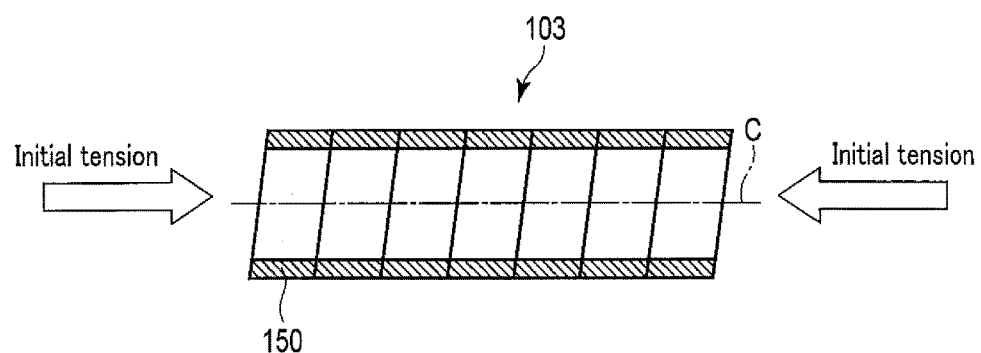
FIG. 5A is a schematic longitudinal cross-sectional view showing a state where an initial tension is given to a densely wound portion of the helical tube to maintain a straight state of the densely wound portion.

As shown in FIG. 5A, the initial tension indicates a force that acts in a direction in which edge portions of the thin plate members 150 of the densely wound portion 103 are brought into contact closely with each other in the central axis C direction of the densely wound portion 103. In other words, the initial tension indicates a force (a preload) with which a state where the edge portions of the thin plate members 150 of the densely wound portion 103 are in contact closely with each other is maintained and the densely wound portion 103 is hard to bend and maintains a substantially linear state against the external force F (e.g., gravity), when, for example, the central axis C of the densely wound portion 103 is horizontally disposed. The initial tension indicates a force (a preload) with which the state where the edge portions of the thin plate members 150 of the densely wound portion 103 are in contact closely with each other is maintained against gravity and the thin plate members 150 are maintained so that no clearance portion is generated between the thin plate members 150, when, for example, the central axis C of the densely wound portion 103 is vertically disposed.

Additionally, in particular, when the initial tension is defined as such "a force to maintain the state where the edge portions of the thin plate members 150 are brought into contact closely with each other" as described above and that is applied to the whole densely wound portion 103, especially the force to be applied to each of the edge portions of the adjacent thin plate members 150 and to bring the edge portions into contact closely with each other can be defined as a close contact force.

For example, the external force F is applied toward the central axis C in a state where, for example, the central axis C of the densely wound portion 103 is horizontally disposed as shown in FIG. 5A. At this time, no clearance portion is formed between the thin plate members 150 and no bending occurs in the densely wound portion 103 until the external force F reaches a force to release the close contact force, i.e., until the external force F exceeds the close contact force. On the other hand, when the external force F applied toward the central axis C reaches the force to release the close contact force or more as shown in FIG. 5B, i.e., when the external force F exceeds the close contact force, the clearance portion is formed between the thin plate members 150 which come in close contact with each other, and the bending occurs in the densely wound portion 103. Therefore, a bending rigidity of the helical tube 100 is increased by the close contact force applied to the densely wound portion 103 until the densely wound portion 103 starts bending. When the close contact force is released by the external force F and the densely wound portion 103 starts bending, the helical tube 100 bends in accordance with a spring constant which the helical tube 100 has. Therefore, when the inserting section 20 is inserted into a body cavity (into a lumen), e.g., a large intestine or the like and the densely wound portion 103 is once started to bend, the flexible tube 25 can be bent in such a state that the densely wound portion 103 is not present.

Such initial tension is given to the densely wound portion 103 when the helical tube 100 is formed, i.e., the densely wound portion 103 is manufactured. The initial tension to be given at this time can suitably be adjusted in accordance with, for example, a winding degree of the thin plate member 150.

Here, a length of the cylindrical envelope 300 in the axial direction along the central axis C is substantially unchanged and about the same even in a linear state or a bent state of the envelope 300. Therefore, a length of the central axis C of the helical tube 100 covered by the envelope 300 is also substantially unchanged and about the same even in a linear state or a bent state of the helical tube 100. Consequently, also when the external force F is applied toward the central axis C of the flexible tube 25, the total length of the helical tube 100 hardly changes.

As shown in FIG. 5C, in the axial direction of the helical tube 100 in the linear state, a length of the densely wound portion 103 in a direction along the central axis C is defined as L1, a length of the one loosely wound portion 101 in the direction along the central axis C is defined as L2, a length of the other loosely wound portion 101 in the direction along the central axis C is defined as L3, and a length of the central axis C of the helical tube 100 in the direction along the central axis C is defined as L4. At this time, the following equation is established:

$$L4=L1+L2+L3 \quad \text{Equation (1).}$$

The external force F is applied to the helical tube 100 in a state shown in FIG. 5C from a direction away from the central axis C of the helical tube 100 and the helical tube 100 is bent as shown in FIG. 5D. As shown in FIG. 5D, the thin plate members 150 of an inner circular part R1 maintain an abutting state on each other due to the initial tension to the central axis C of the densely wound portion 103, and the thin plate members 150 of an outer circular part R2 are detached away from each other to the central axis C of the densely wound portion 103. Consequently, the entire length of the central axis C of the densely wound portion 103 elongates by as much as $\Delta T1$. That is, in a case where the densely wound portion 103 is bent, the length of the central axis C of the densely wound portion 103 in the axial direction is $L1+\Delta T1$.

On the other hand, both ends of the helical tube 100 are actually secured to, for example, the reticular tube 200, and hence the total length of the helical tube 100 is unchanged. Therefore, in a case where the densely wound portion 103 elongates, the loosely wound portion 101 needs to contract as compared with the linear state.

Therefore, as shown in FIG. 5D, when the external force F is applied toward the central axis C of the helical tube 100 to bend the densely wound portion 103, the (one) loosely wound portion 101 on a distal end side and the (other) loosely wound portion 101 on a proximal end side contract as compared with the linear state. That is, in the case where the densely wound portion 103 is bent, the length of the distal end side loosely wound portion 101 and the length of the proximal end side loosely wound portion 101 in the direction along the central axis C are $L2-\Delta T2$ and $L3-\Delta T3$.

At this time, as shown in FIG. 5D, when a length of the central axis C of the bent helical tube 100 is defined as L5, the following equation is established:

$$L5=L1+\Delta T1+L2-\Delta T2+L3-\Delta T3 \quad \text{Equation (2).}$$

Here, as described above, the length of the central axis C of the helical tube 100 needs to be unchanged and the same even in the linear state or the bent state of the helical tube 100, because both ends of the helical tube 100 are secured to, for example, the reticular tube 200. That is, the following equation needs to be established:

$$L4=L5 \quad \text{Equation (3).}$$

When Equations (1) and (2) mentioned above are substituted into Equation (3), the following equation is obtained:

$$L1+L2+L3=L1+\Delta T1+L2-\Delta T2+L3-\Delta T3,$$

and the following equation is established:

$$\Delta T1=\Delta T2+\Delta T3 \quad \text{Equation (4).}$$

In other words, Equation (4) becomes as follows:
Elongation amount of the densely wound portion 103="contraction amount of one loosely wound portion 101"+"contraction amount of the other loosely wound portion 101".

In this way, the elongation amount of the densely wound portion 103 is equal to a contraction amount obtained by adding the contraction amounts of the respective loosely wound portions 101, and the loosely wound portion 101 contracts as much as the amount by which the densely wound portion 103 elongates. That is, when the flexible tube 25 bends, the loosely wound portion 101 absorbs the elongation of the helical tube 100 in the direction along the central axis C which accompanies the elongation of the densely wound portion 103 in the direction along the central axis C in the axial direction of the helical tube 100. Therefore, the loosely wound portions 101 offset the elongation of the helical tube 100 in the direction along the central axis C. Thus, the loosely wound portions 101 are present, whereby the flexible tube 25 can smoothly be bent in a state where characteristics of the densely wound portions 103 having high spring properties to the loosely wound portions 101 are maintained.

[Operation]

As shown in FIG. 2A, FIG. 2B and FIG. 4A, in the present embodiment, the helical tube 100 has the loosely wound portions 101 and the densely wound portions 103 to which the initial tension is given. The flexible tube 25 has the helical tube 100.

Further, when the flexible tube 25 is inserted into and removed from the body cavity (the inside of the lumen), e.g., a curving large intestine, the flexible tube 25 receives the external force F from a bent region in the body cavity, and the flexible tube 25 bends as shown in FIG. 6.

At this time, the densely wound portion 103 elongates. Additionally, at this time, in the inhibition mechanism 500, the outer diameter OD1 is larger than the outer diameter OD2 and the part frictional force F1 is larger than the other part frictional force F2. Consequently, the part 501 inhibits the loosely wound portion 101 from moving to the reticular tube 200 in the axial direction of the helical tube 100. In detail, the part 501 inhibits the loosely wound portion 101 from sliding in the reticular tube 200 in the axial direction of the helical tube 100. Consequently, a relative position of the loosely wound portion 101 to the reticular tube 200 is inhibited from shifting in the axial direction of the helical tube 100. That is, the part 501 functions as a stopper. Therefore, as described above, the loosely wound portion 101 securely contracts to absorb the elongation of the densely wound portion 103.

In consequence, occurrence of a phenomenon where the helical tube 100 does not bend at a definite radius or more is securely prevented. Further, the flexible tube 25 securely and smoothly bends.

Consequently, the flexible tube 25 is easy to be inserted and removed along, for example, the curving large intestine, and the flexible tube 25 is easy to be inserted into and removed from the body cavity. In consequence, insertion-removal properties of the flexible tube 25 improve.

Additionally, at this time, the flexible tube 25 bends, and hence also when the flexible tube abuts on the large intestine that bends, the large intestine is not strongly pressed, high tension is not given to the large intestine and burdens are not loaded onto a patient.

As described above, the relative position of the loosely wound portion 101 to the reticular tube 200 is prevented from shifting in the axial direction of the helical tube 100. Therefore, when the external force F is not applied, the whole flexible tube 25 returns to the linear state due to the densely wound portions 103 having the initial tension.

As described above, in the helical tube 100, the elasticity of the densely wound portion 103 is strong due to the initial tension, and the elasticity of the loosely wound portion 101 is low. Therefore, when the whole flexible tube 25 receives the external force F from the bent region in the body cavity, the densely wound portion 103 noticeably pushes up (bounces back) the bent region against the external force F and the loosely wound portion 101 pushes up (bounces back) the bent region a little against the external force F.

Thus, a pushup force varies in the densely wound portion 103 and the loosely wound portion 101, but the helical tube 100 is pressed by the envelope 300 via the reticular tube 200, and hence a substantially uniform pushup force is obtained in the whole helical tube 100. Therefore, the helical tube 100 pushes back the bent region with a substantially uniform force in the whole helical tube 100, and the insertion-removal properties of the flexible tube 25 can be improved.

[Effect]

In this way, according to the present embodiment, the relative position of the loosely wound portion 101 to the reticular tube 200 can be inhibited from shifting in the axial direction of the helical tube 100 by the inhibition mechanism 500 even in a state where the flexible tube 25 has the helical tube 100 having the loosely wound portions 101 and the densely wound portions 103 to which the initial tension is given.

As a result, in the present embodiment, it is possible to securely prevent the occurrence of the phenomenon where the helical tube 100 does not bend at the definite radius or more, and the flexible tube 25 can securely and smoothly be bent.

In the present embodiment, the flexible tube 25 can be easy to be inserted and removed along, for example, the curving large intestine and the flexible tube 25 can be easy to be inserted into and removed from the body cavity. In this way, according to the present embodiment, the insertion-removal properties of the flexible tube 25 can be improved.

In the present embodiment, as described above, the inhibition mechanism 500 can prevent the relative position of the loosely wound portion 101 to the reticular tube 200 from shifting in the axial direction of the helical tube 100. Therefore, in the present embodiment, when the external force F is not applied, the whole flexible tube 25 can be returned to the linear state by the densely wound portions 103 having the initial tension.

In the present embodiment, the helical tube 100 can bounce back the bent region with a substantially uniform force in the whole helical tube 100, and the insertion-removal properties of the flexible tube 25 can be improved.

In the present embodiment, the part 501 may only be adjusted to be larger than the other part 503 so that the outer diameter OD1 is larger than the outer diameter OD2. Therefore, in the present embodiment, the part frictional force F1 can be adjusted to be larger than the other part frictional force F2 by use of a simple configuration. In the present embodiment, the whole flexible tube 25 can be prevented from being thicker, and the insertion-removal properties of the flexible tube 25 can be improved.

In the present embodiment, the part 501 may solely be processed so that the outer diameter OD1 is larger than the outer diameter OD2. Consequently, in the present embodiment, the densely wound portion 103 in the other part 503 does not have to be processed, and attention need only be devoted to providing the initial tension to the densely wound portion 103 when the densely wound portion 103 is processed. Therefore, in the present embodiment, a quality of the flexible tube 25 can be adjusted to be uniform.

In the present embodiment, the part 501 includes, for example, the center portion of the loosely wound portion 101 in the axial direction of the helical tube 100, and indicates, for example, one winding of the thin plate member 150. This indicates that the part 501 is disposed along the whole periphery of the helical tube 100 in a peripheral direction of the helical tube, and disposed in the form of a plane. As described above, the cross-sectional shape of the part 501 is analogous to the cross-sectional shape of the other part 503 so that the cross-sectional shape of the part 501 is larger than the cross-sectional shape of the other part 503.

However, the present invention does not have to be limited to this embodiment. As shown in FIG. 7, for example, the cross-sectional shape of the part 501 may be non-analogous to the cross-sectional shape of the other part 503 so that the part 501 partially swells out from the other part 503 in at least one radial direction. That is, the diameter of the part 501 may be partially larger than that of the other part 503. Consequently, the part 501 is partially disposed in the peripheral direction of the helical tube 100 and disposed in the form of a dot. For example, in a case where the other part 503 has a circular cross section, the part 501 has a larger elliptic cross section than the other part 503.

As described above, the part 501 disposed in the one loosely wound portion 101 and having the enlarged diameter may be disposed on the same straight line as the part 501 disposed in the other loosely wound portion 101 and having the enlarged diameter in the axial direction of the helical tube 100. The part 501 disposed in the one loosely wound portion 101 and having the enlarged diameter may be disposed to shift to the part 501 disposed in the other loosely wound portion 101 and having the enlarged diameter in the peripheral direction of the helical tube 100.

[Modifications]

In the first embodiment, in the inhibition mechanism 500, as one example, the outer diameter OD1 is larger than the outer diameter OD2 so that the part frictional force F1 is larger than the other part frictional force F2. However, the present invention does not have to be limited to this embodiment. This aspect will be described as a modification hereinbelow. Hereinafter, configurations different from the configuration of the first embodiment will only be described. It is to be noted that the same configuration as the configuration of the first embodiment is denoted with the same reference signs, and detailed descriptions are omitted.

[First Modification]

[Configuration]

Figure 8A:
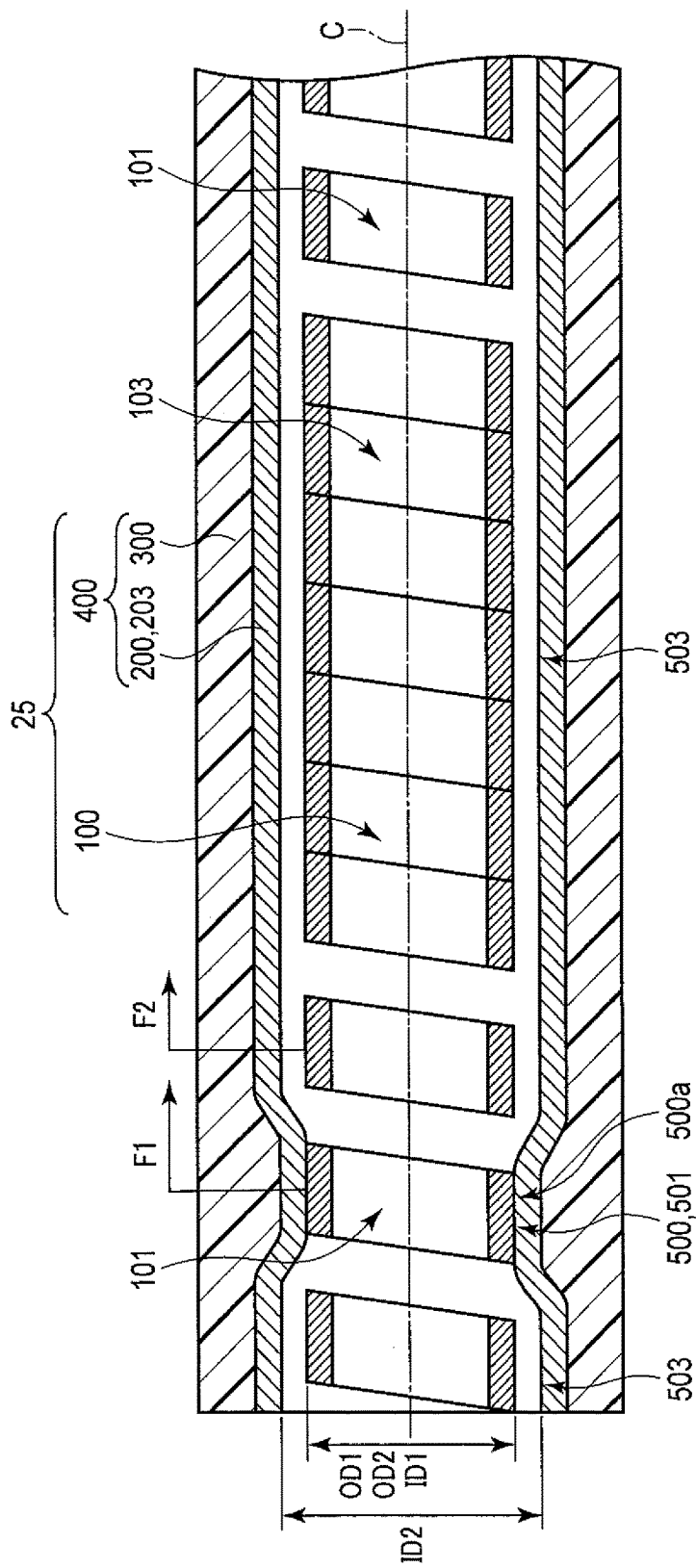
FIG. 8A is a view showing a first modification in which a thickness of a strand bundle is uniform along the whole reticular tube and an inner diameter ID1 is smaller than an inner diameter ID2.
Figure 8B:
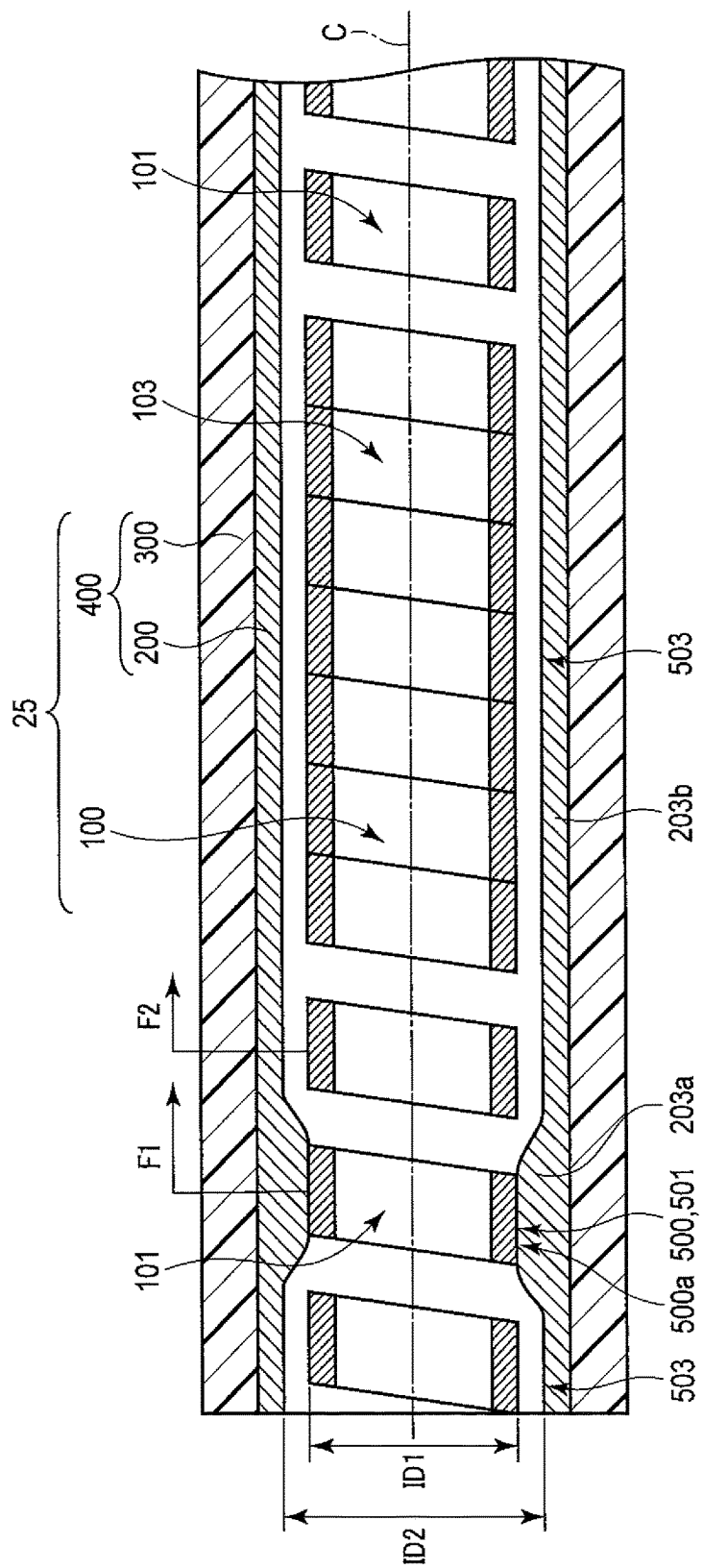
FIG. 8B is a view showing the first modification in which an outer diameter is uniform along the whole reticular tube, but a strand bundle 203a is thicker than a strand bundle 203b so that the inner diameter ID1 is smaller than the inner diameter ID2.
Figure 8C:
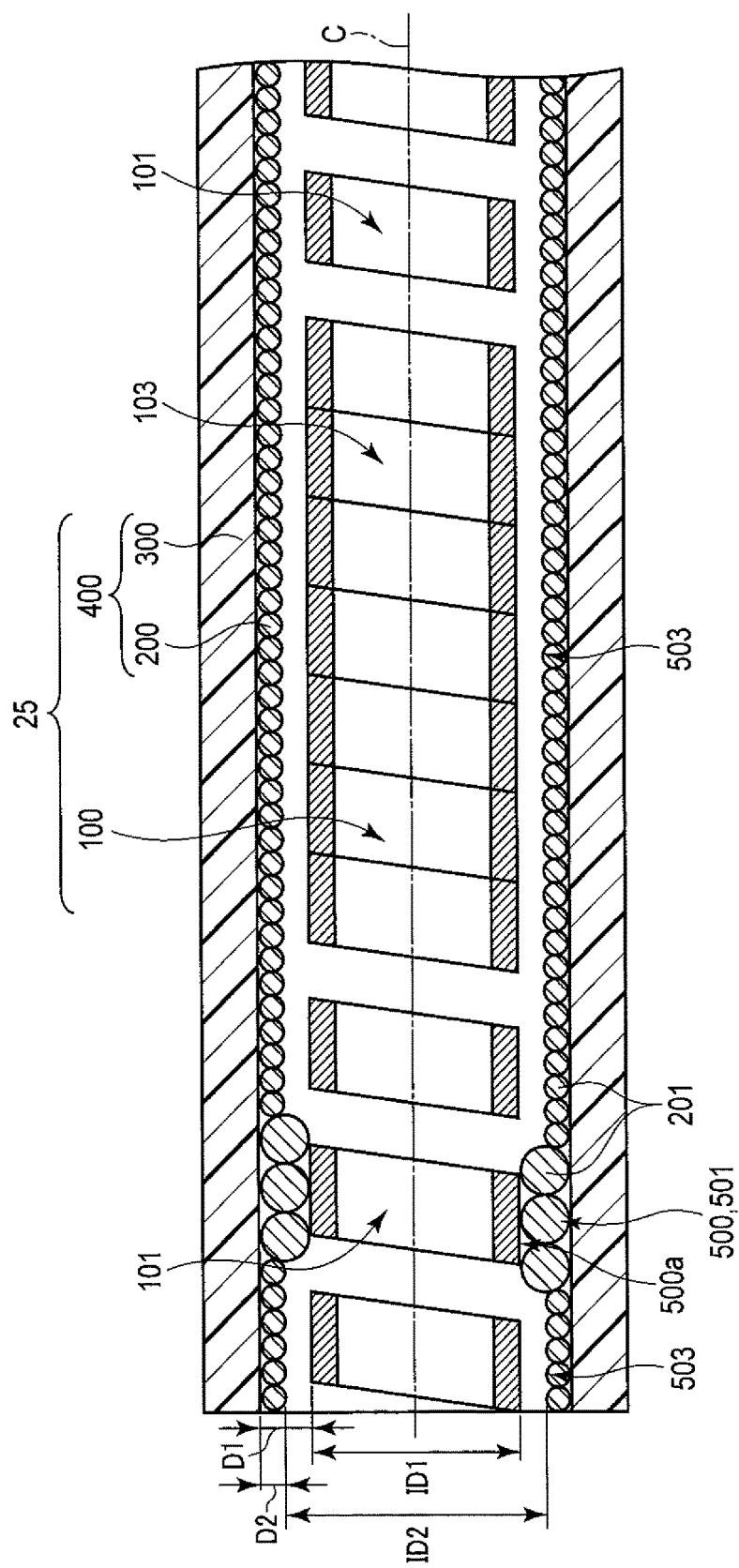
FIG. 8C is a view showing the first modification, and showing that a diameter D1 is larger than a diameter D2.

As shown in FIG. 8A, FIG. 8B and FIG. 8C, an inner diameter ID1 which a cover 400 has in a portion that covers a part 501 is smaller than an inner diameter ID2 which the cover 400 has in a portion that covers another part 503, for example, in a state where an outer diameter OD1 is the same as an outer diameter OD2. In this case, the cover 400 indicates, for example, a reticular tube 200.

In this case, for example, the reticular tube 200 in the portion that covers the part 501 abuts on the part 501 and the reticular tube 200 in the portion that covers the other part 503 does not abut on the other part 503. In consequence, a part frictional force F1 is generated, but another part frictional force F2 is not generated, and the part frictional force F1 is larger than the other part frictional force F2 that is zero. Therefore, the part frictional force F1 becomes larger than the other part frictional force F2.

The inner diameter ID1 which the reticular tube 200 has in the portion that covers the part 501 is smaller than the inner diameter ID2 which the reticular tube 200 has in the portion that covers the other part 503, for which, e.g., A, B and C mentioned below are considered.

A (See FIG. 8A)

A thickness of a strand bundle 203 is uniform along the whole reticular tube 200, and the inner diameter ID1 is smaller than the inner diameter ID2.

B (See FIG. BB):

The strand bundle 203 in the reticular tube 200 in the portion that covers the part 501 is referred to as a strand bundle 203a.

The strand bundle 203 in the reticular tube 200 in the portion that covers the other part 503 is referred to as a strand bundle 203b.

An outer diameter of the reticular tube 200 is uniform along the whole reticular tube 200, but the strand bundle 203a is thicker than the strand bundle 203b so that the inner diameter ID1 is smaller than the inner diameter ID2.

C (See FIG. 8C):

A diameter of each strand 201 in the reticular tube 200 in the portion that covers the part 501 is referred to as a diameter D1.

A diameter of the strand 201 in the reticular tube 200 in the portion that covers the other part 503 is referred to as a diameter D2.

The diameter D1 is larger than the diameter D2.

[Effect]

In the present modification, the outer diameter OD1 does not have to be larger than the outer diameter OD2 as in the first embodiment, but an outer diameter of a helical tube 100 can be uniform, and the helical tube 100 can easily be manufactured. In the present modification, the reticular tube 200 may only be manufactured as described above, and hence the total manufacturing cost of the endoscope can be reduced.

It is to be noted that in the present modification, as described above, a clearance portion is disposed between the reticular tube 200 and the other part 503, in the other part 503 for clarification of the drawing, but the present invention is not limited to this example. For example, an envelope 300 may press the reticular tube 200 in the portion that covers the part 501, toward the part 501, and may press the reticular tube 200 in the portion that covers the other part 503, toward the other part 503. Consequently, the reticular tube 200 in the portion that covers the part 501 abuts on the part 501 and the reticular tube 200 in the portion that covers the other part 503 abuts on the other part 503. However, the inner diameter ID1 which the reticular tube 200 in the portion that covers the part 501 has is smaller than the inner diameter ID2 which the reticular tube 200 in the portion that covers the other part 503 has, and hence an amount of a force to be applied from the reticular tube 200 to the part 501 is larger than an amount of a force to be applied from the reticular tube 200 to the other part 503. Therefore, the part frictional force F1 is larger than the other part frictional force F2.

A density of the strand bundle 203 in the reticular tube 200 in the portion that covers the part 501 may be larger than a density of the strand bundle 203 in the reticular tube 200 in the portion that covers the other part 503. Consequently, the reticular tube 200 is in more contact with the part 501 than the other part 503. Therefore, the part frictional force F1 is larger than the other part frictional force F2.

In the above, the description concerns the reticular tube 200, but the description could equally refer to the envelope 300.

[Second Modification]
[Configuration]

In an envelope 300, a resin material penetrates into a reticular tube 200 in a portion that covers a part 501 more than the reticular tube 200 in a portion that covers another part 503. Further, the resin material abuts on an outer peripheral surface of the part 501 and an outer peripheral surface of the other part 503 via the reticular tube 200. At this time, the resin material abuts on the outer peripheral surface of the part 501 more than the outer peripheral surface of the other part 503. At this time, for example, the resin material may be bonded.

Therefore, a part frictional force F1 is larger than another part frictional force F2.

[Effect]

In the present modification, the envelope 300 only be manufactured as described above, and hence the total manufacturing cost of the endoscope can be reduced.

[Third Modification]
[Configuration]

An outer peripheral surface of a part 501 is rougher than an outer peripheral surface of another part 503.

An inner peripheral surface of a cover 400 in a portion that covers the outer peripheral surface of the part 501 is rougher than the inner peripheral surface of the cover 400 in a portion that covers the outer peripheral surface of the other part 503.

The outer peripheral surface of the part 501 is roughened by, for example, blast processing. This aspect is also similar to the inner peripheral surface of the cover 400 in the portion that covers the outer peripheral surface of the part 501. The roughening may be performed on at least one of the outer peripheral surface of the part 501 and the inner peripheral surface of the cover 400 in the portion that covers the outer peripheral surface of the part 501.

Therefore, a part frictional force F1 is larger than another part frictional force F2.

It is to be noted that in the present modification, the cover 400 indicates, for example, a reticular tube 200.

[Effect]

In the present modification, at least one of the outer peripheral surface and the inner peripheral surface may only be processed, and hence the total manufacturing cost of the endoscope can be reduced.

[Fourth Modification]
[Configuration]

Figure 9:
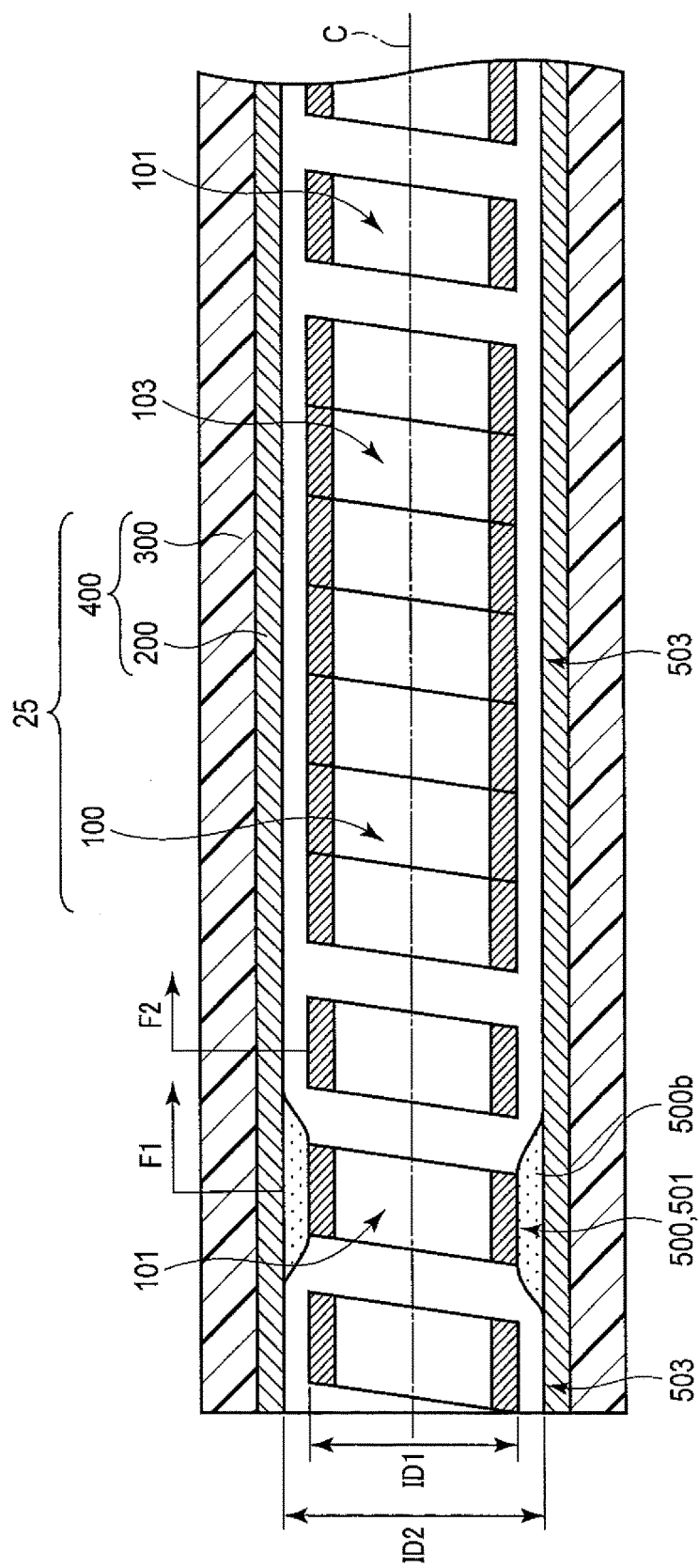
FIG. 9 is a view showing a fourth modification, and showing that a fixing section is disposed.

As shown in FIG. 9, an inhibition mechanism 500 further has a fixing section 500b that fixes a part 501 of at least one loosely wound portion 101 to at least a part of a cover 400 in a portion that covers the part 501. The fixing section 500b includes, for example, bonding. It is to be noted that the present invention does not have to be limited to this example, and the fixing section 500b includes at least one of soldering, string binding, and bonding. The fixing may be performed only in one region of the part 501, along the whole periphery of the part 501, or in discontinuous parts in a peripheral direction. The fixing may be performed in parts of the one loosely wound portion 101.

[Effect]

In the present modification, the part 501 of the loosely wound portion 101 is fixed to the cover 400. Consequently, even when an inserting section 20 is twisted, a helical tube including the loosely wound portion 101 can follow this twist. Therefore, in the present modification, a relative position of the loosely wound portion 101 to a reticular tube 200 in a peripheral direction of the helical tube can be inhibited from shifting.

[Fifth Modification]
[Configuration]
[Passive Bending Section 24]

Figure 10:
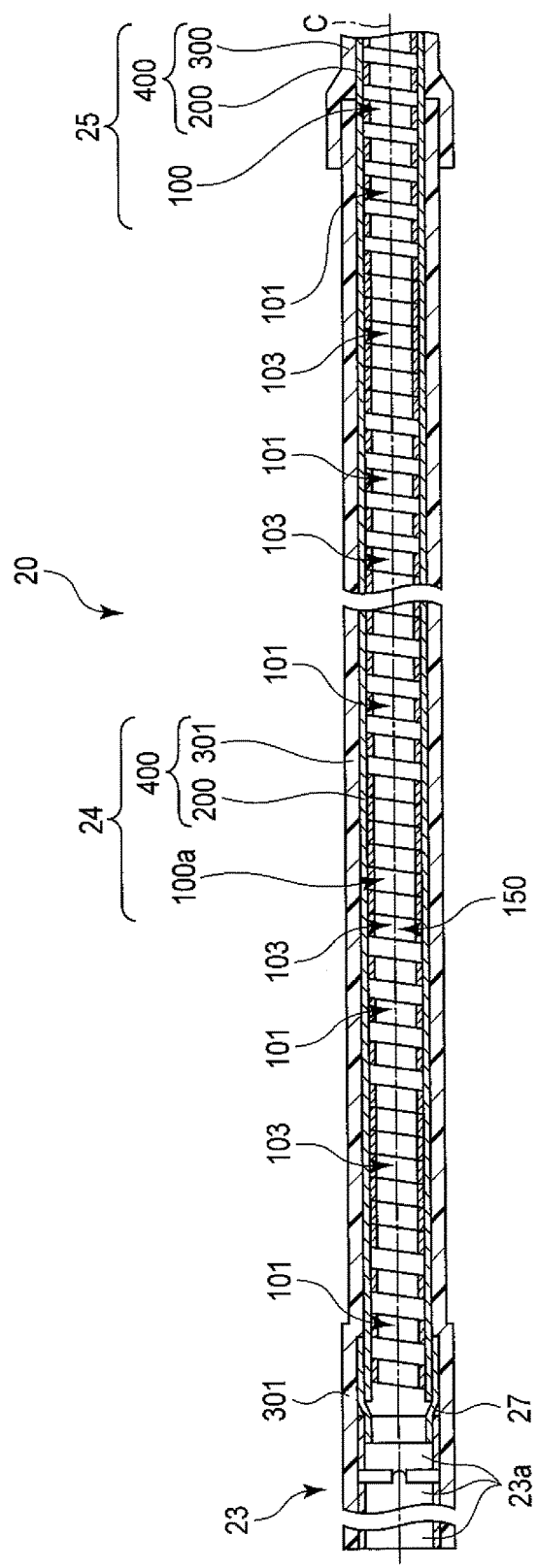
FIG. 10 is a schematic longitudinal cross-sectional view showing a fifth modification, and showing a structure of a flexible tube, a passive bending section and a bending section.

As shown in FIG. 10, an inserting section 20 may further have a passive bending section 24 disposed between a bending section 23 and a flexible tube 25 in a central axis C direction of the inserting section 20. The passive bending section 24 has a distal end portion to be coupled with the bending section 23 and a proximal end portion to be coupled with the flexible tube 25. As described above, the distal end portion of the passive bending section 24 is coupled with node rings 23a disposed in a proximal end portion of the bending section 23 via a coupling member 27 such as a mouthpiece. The proximal end portion of the passive bending section 24 is coupled with a distal end portion of the flexible tube 25.

The passive bending section 24 has a desirable flexibility. Therefore, the passive bending section 24 passively bends by receiving an external force F. This external force F indicates, for example, a force to be applied to the passive bending section 24 at a desirable angle to a central axis of the passive bending section 24 (the central axis C of the inserting section 20).

[Relations Among Bending Section 23, Passive Bending Section 24 and Flexible Tube 25]

The bending section 23 is mainly configurated of the node rings 23a as described above.

On the other hand, as shown in FIG. 10, the passive bending section 24 is not configurated of the node rings 23a, and details will be described later, but the passive bending section is mainly configurated of a helical tube 100a. In this way, the passive bending section 24 is a separate member from the bending section 23.

As shown in FIG. 10, the helical tube 100a of the passive bending section 24 and a helical tube 100 of the flexible tube 25 are integrally formed of the same helical thin plate member 150. For the sake of convenience, to distinguish from the helical tube 100, the helical tube of the passive bending section 24 is denoted with a reference sign of the helical tube 100a. Therefore, a distal end portion of the thin plate member 150 functions as the helical tube 100a of the passive bending section 24, and a proximal end portion of the thin plate member 150 functions as the helical tube 100 of the flexible tube 25. In this way, the helical tube 100a of the passive bending section 24 and the helical tube 100 of the flexible tube 25 are the same as each other, connected to each other, and integrated with each other. Therefore, the passive bending section 24 can function as the distal end portion of the flexible tube 25.

It is to be noted that the helical tube 100a of the passive bending section 24 may be a separate member from the helical tube 100 of the flexible tube 25, as long as the helical tube of the passive bending section is connected to the helical tube 100 of the flexible tube 25.

In this way, the helical tube 100a of the passive bending section 24 may be continuous with the helical tube 100 of the flexible tube 25.

[Member Shared by Passive Bending Section 24 and Flexible Tube 25, and Member Peculiar to Passive Bending Section 24]

As shown in FIG. 10, the passive bending section 24 has, for example, a hollow shape. The passive bending section 24 has the helical tube 100a shared by the flexible tube 25 as described above, a reticular tube 200 shared by the flexible tube 25, and an envelope 301 that is different from an envelope 300 of the flexible tube 25 and is peculiar to the passive bending section 24.

The reticular tube 200 covers an outer peripheral surface of the helical tube 100a so that the reticular tube 200 abuts on the outer peripheral surface of the helical tube 100a. The envelope 301 covers an outer peripheral surface of the reticular tube 200 so that the envelope 301 abuts on the outer peripheral surface of the reticular tube 200. The reticular tube 200 is laminated on the helical tube 100 and the envelope 301 is laminated on the reticular tube 200.

In this way, the passive bending section 24 is configured of the helical tube 100a, the reticular tube 200 and the envelope 301, and consequently, the passive bending section 24 has a three-layer structure by those.

It is to be noted that the reticular tube 200 does not necessarily have to be disposed. Therefore, the passive bending section 24 may be configurated of at least the helical tube 100 and the envelope 301, and consequently, the passive bending section 24 may have a two-layer structure by those.

Therefore, the passive bending section 24 may have the helical tube 100, and a cover 400 that covers the outer peripheral surface of the helical tube 100 so that the cover 400 abuts on the outer peripheral surface of the helical tube 100. The cover 400 has, for example, at least the envelope 301.

[Helical Tube 100a]

As described above, the helical tube 100a of the passive bending section 24 and the helical tube 100 of the flexible tube 25 are not separate members from each other but are the same as each other. In this way, one helical tube 100 is shared by the passive bending section 24 and the flexible tube 25. That is, the helical tube 100 is continuously integrally disposed in the passive bending section 24 and the flexible tube 25.

The helical tube 100a has loosely wound portions 101 and densely wound portions 103 similarly to the helical tube 100.

An inhibition mechanism 500 may not be disposed in the helical tube 100a.

[Reticular Tube 200]

As shown in FIG. 10, the reticular tube 200 that covers the helical tube 100a and a reticular tube 200 that covers the helical tube 100 are not separate members from each other, but are the same members as each other, and are integral with each other. In other words, the reticular tube 200 that covers the helical tube 100 is extended from the passive bending section 24 to the flexible tube 25 to cover the helical tube 100a. In this way, the helical tube 100 and the helical tube 100a are covered with one common reticular tube 200. That is, the one reticular tube 200 is shared by the passive bending section 24 and the flexible tube 25. In other words, the reticular tube 200 is continuously integrally disposed in the passive bending section 24 and the flexible tube 25.

It is to be noted that the reticular tube 200 of the passive bending section 24 may be a separate member from the reticular tube 200 of the flexible tube 25 as long as the reticular tube of the passive bending section is integrally connected to the reticular tube 200 of the flexible tube 25.

In this way, the reticular tube 200 of the passive bending section 24 may be continuous with the reticular tube 200 of the flexible tube 25.

[Envelope 301]

The envelope 301 is made of, for example, a resin. The envelope 301 covers the reticular tube 200 in the passive bending section 24 and also covers the bending section 23. In detail, the envelope 301 covers the node rings 23a in the bending section 23. Therefore, the envelope 301 integrally covers the passive bending section 24 and the bending section 23.

In this way, the envelope 301 that covers the reticular tube 200 in the passive bending section 24 is extended from the passive bending section 24 to the bending section 23, and covers an outer peripheral surface of the bending section 23 so that the envelope abut on the outer peripheral surface of the bending section 23. Further, the reticular tube 200 in the passive bending section 24 and the node rings 23*a* in the bending section 23 are covered with one common envelope 301. That is, the one envelope 301 is shared by the passive bending section 24 and the bending section 23. In other words, the envelope 301 is continuously integrally disposed in the passive bending section 24 and the bending section 23.

It is to be noted that the envelope 301 may be a separate member from the envelope that covers the bending section 23.

A proximal end portion of the envelope 301 is covered with a distal end portion of the envelope 300.

[Conclusions]

In the abovementioned embodiment and the respective modifications, the helical tube 100 of the flexible tube 25 has been described by using the relation between at least a part 501 of the loosely wound portion 101 and another part, i.e., between each of the parts 501 and each of the other parts 503 (the other parts of the loosely wound portions 101 and the densely wound portions 103) except for the parts 501 in the helical tube 100. However, this relation does not have to be limited to this example.

For example, the part 501 of the loosely wound portion 101 may indicate the whole loosely wound portion 101 and the other part 503 of the helical tube 100 may indicate the whole densely wound portion 103. That is, the abovementioned relation may be applied to the loosely wound portion 101 and the densely wound portion 103.

The abovementioned relation may be applied to, for example, the part 501 of the loosely wound portion 101 and the other part of the loosely wound portion 101.

When the loosely wound portions 101 are surely disposed in the distal end portion of the helical tube 100 and the proximal end portion of the helical tube 100, the loosely wound portions 101 and the densely wound portions 103 do not have to be alternately arranged along the whole flexible tube 25. The loosely wound portions 101 and the densely wound portions 103 may alternately be arranged in a desirable portion of the flexible tube 25, e.g., the distal end portion of the helical tube 100.

The present invention is not limited to the above embodiment as it is, and configurational elements can be modified and embodied without departing from the gist in an implementing stage of the invention. Additionally, various inventions can be formed by any suitable combination of the configurational elements described in the above embodiment.

What is claimed is:

1. A flexible tube for an endoscope, comprising:
   a helical tube comprising a thin plate that is helically wound along a central axis such that the helical tube comprises:
      loosely wound portions in which adjacent turns of the thin plate are spaced apart from each other in a direction of the central axis; and
      densely wound portions in which adjacent turns of the thin plate are in contact with each other in the direction of the central axis;
   a cylindrical cover that covers an outer peripheral surface of the helical tube and has flexibility; and
   an inhibition mechanism that enables movement of at least one of the densely wound portions relative to the cover in the direction of the central axis and inhibits movement of at least one of the loosely wound portions relative to the cover in the direction of the central axis, wherein
   the loosely wound portions and the densely wound portions are alternatively disposed in the direction of the central axis;
   the thin plate is under an initial tension in the densely wound portions;
   the initial tension is an internal force that is applied against the densely wound portions in the direction of the central axis to keep the adjacent turns of the thin plate in contact with each other in the absence of an external force that is greater than the internal force;
   a first part of the helical tube has an outer diameter that is larger than an outer diameter of a second part of the helical tube; and
   the first part includes at least part of a loosely wound portion disposed in a distal end of the helical tube.

2. The flexible tube according to claim 1, wherein the inhibition mechanism inhibits a center portion of the at least one loosely wound portion in the direction of the central axis from moving relative to the cover in the direction of the central axis.

3. The flexible tube according to claim 2, wherein
   the inhibition mechanism has a first part frictional force generating section that generates a part frictional force between an outer peripheral surface of the first part and an inner peripheral surface of the cover which abuts on the outer peripheral surface of the first part, and
   the first part frictional force is larger than a second part frictional force generated between an outer peripheral surface of the second part of the helical tube and the inner peripheral surface of the cover which abuts on the outer peripheral surface of the second part.

4. The flexible tube according to claim 3, wherein
   the cover comprises a reticular tube that covers the outer peripheral surface of the helical tube, and an envelope that covers an outer peripheral surface of the reticular tube;
   the envelope is made of a resin material, and
   the resin material penetrates into a portion of the reticular tube that covers the first part of the helical tube more than the resin material penetrates into a portion of the reticular tube that covers the second part, and abuts on the outer peripheral surface of the first part of the helical tube more than the outer peripheral surface of the second part of the helical tube.

5. The flexible tube according to claim 3, wherein the outer peripheral surface of the first part of the helical tube is rougher than the outer peripheral surface of the second part of the helical tube.

6. The flexible tube according to claim 3, wherein an inner peripheral surface of a portion of the cover that covers the outer peripheral surface of the first part of the helical tube is rougher than an inner peripheral surface of a portion of the cover that covers the outer peripheral surface of the second part of the helical tube.

7. The flexible tube according to claim 2, wherein the inhibition mechanism further has a fixing section that fixes the first part of the helical tube to a portion of the cover that covers the first part of the helical tube.

8. The flexible tube according to claim 7, wherein the fixing section includes at least one of soldering, string binding, and bonding.

9. An endoscope comprising the flexible tube according to claim 1, and a bending section that is coupled to a distal end of the flexible tube.

10. The flexible tube according to claim 1, wherein the first part further includes at least part of a loosely wound portion disposed in a proximal end of the helical tube.

11. The flexible tube according to claim 1, wherein the first part includes at least a part of each of the loosely wound portions.

12. The flexible tube according to claim 1, wherein the first part further includes at least a center portion of a loosely wound portion in the direction of the central axis of the helical tube.

13. The flexible tube according to claim 1, wherein the second part includes a part of a loosely wound portion and all of a densely wound portion.

* * * * *